United States Patent [19]

Chappuis et al.

[11] Patent Number: 5,653,729
[45] Date of Patent: Aug. 5, 1997

[54] MEDICAL INSTRUMENT WITH RELEASABLE LOCK

[75] Inventors: Michael C. Chappuis, Bloomington; Robert C. Collins, Eden Prairie, both of Minn.

[73] Assignee: InnoMedica

[21] Appl. No.: 595,233

[22] Filed: Feb. 1, 1996

[51] Int. Cl.⁶ .................. A61B 17/12; A61B 17/28
[52] U.S. Cl. ............................ 606/207; 606/205
[58] Field of Search ...................... 606/208, 205, 606/206, 207, 210–211; 292/303; 24/518, 543

[56] References Cited

U.S. PATENT DOCUMENTS

| | | | |
|---|---|---|---|
| 3,654,930 | 4/1972 | Hobbs, II ........................ | 606/208 |
| 3,911,766 | 10/1975 | Fridolph et al. ................ | 606/208 X |
| 4,432,352 | 2/1984 | Wineland ......................... | 606/208 X |
| 4,461,297 | 7/1984 | Sutter ............................... | 606/210 X |
| 4,462,404 | 7/1984 | Schwarz et al. ................ | 606/206 X |
| 4,646,755 | 3/1987 | Kane . | |
| 4,722,339 | 2/1988 | Dreier et al. ..................... | 606/208 X |
| 4,823,792 | 4/1989 | Dulebohn et al. ............... | 606/208 X |
| 4,917,677 | 4/1990 | McCarthy . | |
| 4,972,847 | 11/1990 | Dutcher et al. . | |
| 5,040,545 | 8/1991 | Dutcher et al. . | |
| 5,143,090 | 9/1992 | Dutcher et al. . | |
| 5,156,431 | 10/1992 | Lowe ................................ | 606/210 X |
| 5,196,023 | 3/1993 | Martin . | |
| 5,217,028 | 6/1993 | Dutcher et al. . | |
| 5,236,436 | 8/1993 | Koros et al. . | |
| 5,250,072 | 10/1993 | Jain . | |
| 5,255,693 | 10/1993 | Dutcher et al. . | |
| 5,304,188 | 4/1994 | Marogil . | |
| 5,368,596 | 11/1994 | Burkhart ......................... | 606/208 X |

FOREIGN PATENT DOCUMENTS 0065432  7/1996  Switzerland ..................... 606/208

*Primary Examiner*—Michael Buiz
*Assistant Examiner*—Nancy Connolly Mulcare
*Attorney, Agent, or Firm*—Palmatier, Sjoquist, Helget & Voigt, P.A.

[57] ABSTRACT

An improved medical instrument with a releasable lock interposed between the handles of the needle holder to hold the jaws in closed position to grip an object. The lock has flexible fingers and a plurality of movable sleeves that allow one hand operation to selectively lock and release the jaws without substantial lateral displacement of the object. A plurality of locking stops is provided so that the jaws may be held closed at a variety to tensions, to accommodate a variety of objects.

23 Claims, 2 Drawing Sheets

MEDICAL INSTRUMENT WITH RELEASABLE LOCK

BACKGROUND OF THE INVENTION

The invention relates to medical instruments having jaws for clamping, grasping, or holding medical devices and/or portions of an individual's anatomy.

Conventional medical instruments (needle holders, forceps, etc.) may be used by a physician to manipulate the handles to hold and work the grasping jaws for various medical procedures. Conventional forceps and needle holders are fabricated from a pair of rigid parts each having a jaw at one end and a handle with a ring at the other end. The two parts are mounted together to form a scissors-like instrument. The two parts are pivotally secured behind the pair of jaws. There is a finger ring and a thumb ring at the distal end of each handle. The physician places his thumb in one ring and his index finger in the other ring to control and manipulate the tool or instrument. He can squeeze the two rings together with his thumb and finger to cause the jaws to clamp down. The conventional forceps requires squeezing of the handle while simultaneously manipulating the forceps. Some instruments have engageable snap together locking means on the pair of handles and towards the rings to lock the jaws shut by locking the pair of handles together. It is usually a snap connection. The lock will engage when sufficient force is supplied by the finger and thumb to press the rings together. The lock will disengage when sufficient force is applied to spread apart the rings.

The disadvantage of this type of locking instrument is that substantial side force must be used to unlock the handles. Sometimes, this requires the use of two hands. If one hand is used to spread apart the rings, the forceps may suddenly move laterally as the rings disengage, potentially causing collateral damage or puncture of a delicate organ. Physicians often need the other hand for holding onto the skin or organ and cannot spare that hand to help to disengage the clamped instrument.

There is a need for medical instruments with an improved locking arrangement which allows the physician to lock and unlock the instrument using only one hand, and without imposing any side-to-side motion of the instrument as the jaws unlock.

Medical instruments come in various sizes and are used for particular medical procedures. Thus, a medical instrument must be capable of clamping onto a variety of objects including, but not limited to surgical needles, vessels, and/or organs. There is thus a need for a tension adjustment for the jaws of the medical instrument. The tension must be adjustable with only one hand.

SUMMARY OF THE INVENTION

An improved medical instrument with a releasable lock interposed between the handles of the instrument to hold the jaws in closed position to grip the desired object. The lock has flexible fingers and a plurality of movable sleeves that allow one hand operation to selectively lock and release the jaws without substantial lateral displacement. A plurality of locking stops is provided so that the jaws may be held closed at a variety of tensions, to accommodate a variety of objects.

A principal object of the invention is to provide an instrument which allows a physician to lock and unlock the instrument onto the object using only one hand, and without imposing any side-to-side motion of the instrument as the jaws unlock.

A second principal object of the invention is to provide a tension adjustment, operable by one hand, for clamping the instrument onto a variety of objects of various sizes.

A feature of the present invention includes a releasable locking device interposed between the handles permitting one-handed tension adjustment of the medical instrument.

Another feature of the present invention is a locking mechanism including flexible fingers and a plurality of movable sleeves permitting one-handed operation of the medical instrument.

Still another feature of the present invention is a plurality of locking stops adapted for engagement to the flexible fingers permitting the locking of the jaws at a variety of tensions to accommodate a variety of objects.

DETAILED DESCRIPTION OF THE PREFERRED EMBODIMENTS

Figure 1:
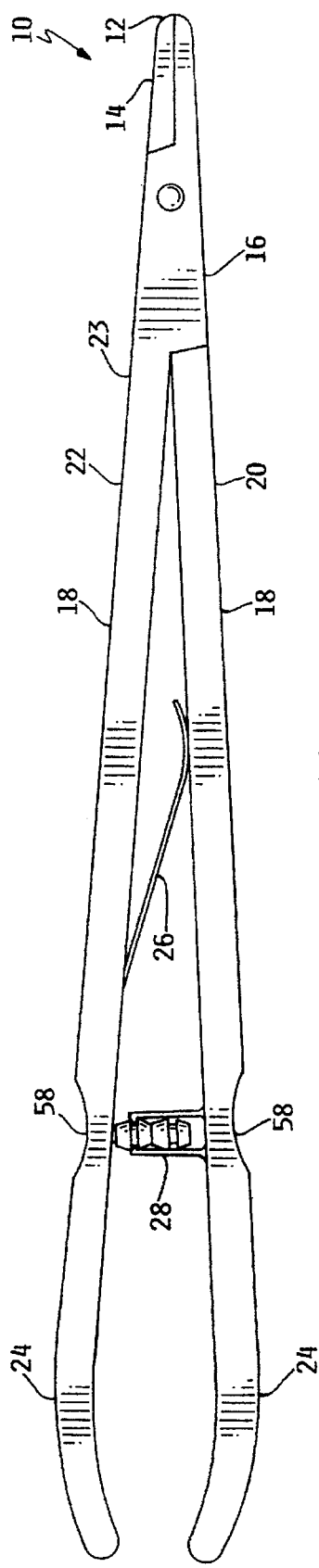
FIG. 1 is a plan view of a surgical needle holder which is one example of a medical instrument.

FIG. 1 shows a medical instrument 10 employing the present invention. FIG. 1 shows an example of a needle holder without finger and thumb rings. The needle holder 10 comprises a pair of pivotally-connected scissor jaws 12. The jaws 12 have jaw ends 14 for grasping a surgical needle and thread, and attachment ends 16.

A pair of spaced apart angularly opposed handle bodies 18, comprising a first handle 20 and a second handle 22, have first ends 23 and second ends 24. The first ends 23 may be secured in tandem with the attachment ends 16 of the jaws 12, thereby operating the jaws.

A spring may be located approximately midway between the first ends 23 and the second ends 24. The spring 26 is preferably attached to one of the handle bodies 18 and biases against the other handle body 18. The spring 26 preferably functions to keep the handle bodies 18 spread apart and the jaws 12 open when at the at-rest position.

The medical instrument 10 may also include a releasable lock means 28 mounted between the handle bodies 18. As will be seen, a physician may operate the lock means 28 with one hand, either to lock a needle into the holder 10 or to release the lock means 28 to remove a needle from the needle holder 10. The releasable lock means 28 described herein may also function to selectively connect and release any two members at a series of spaced positions relative to each other.

The releasable lock means 28 further comprises a first means 30 secured to the first handle 20 and a second means 32 secured to the second handle 22. A releasable cooperating means 34 preferably holds the first handle 20 and second handle 22 adjacent each other, thereby retaining the jaws 12 in the closed position. The releasable cooperating means 34 also operates to release the first means 30 and second means 32, thus allowing the first handle 20 and second handle 22 to move away from each other and the jaws 12 to move to the open position.

In one embodiment, the first means 30 includes finger means 36 secured to the first handle 20. The second means 32 includes holding means 38 engageable with the finger means 36 to hold the first handle 20 and second handle 22 adjacent each other. The cooperating means 34 includes sliding means 35 to release the finger means 36 from the holding means 38, allowing the first handle 20 and second handle 22 to move away from each other and the jaws 12 to move to the open position.

In another embodiment, the finger means 36 comprises a pair of flexible fingers 40 having hooks 42. The holding means 38 may include a head 39 engageable with the hooks 42 to hold the first handle 20 and second handle 22 adjacent each other. The operating means 34 operates to release the hooks 42 from the head 39 when the first handle 20 and second handle 22 are moved toward each other.

In another embodiment, the holding means 38 comprises a plurality of heads 39 and a plurality of cooperating means 34. This arrangement forms a tension adjustment which allows the first handle 20 and second handle 22 to be moved towards each other in a series of steps thereby locking the jaws 12 closer and closer together. With this tension adjustment, the needle holder 10 may be used to tightly hold needles with varying thicknesses without bending the needles. The cooperating means 34 operates to release the hooks 42 from all heads 39 when the first handle 20 and second handle 22 are moved toward each other.

The heads 39 may be mounted on a projection 44 secured to the second handle 22. Surrounding the projection 44 may be movable sleeve means 46 which are the sliding means 35 to release the finger means 36. The hooks 42 engage a shoulder 48 on the head 39 to hold the first handle 20 and second handle 22 adjacent each other. The sleeve means 46 are may be spaced from the shoulder 48 to allow the hooks 42 to engage the shoulder 48.

Figure 2:
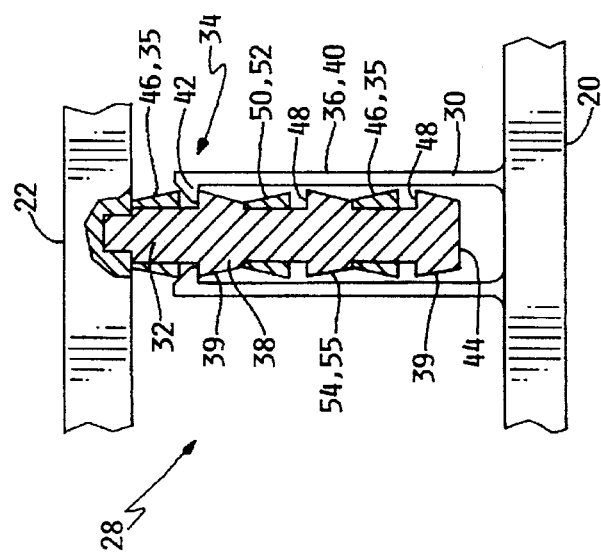
FIG. 2 is a detail of the locking mechanism partially broken away, showing the locking mechanism in the locked position at highest tension.
Figure 4:
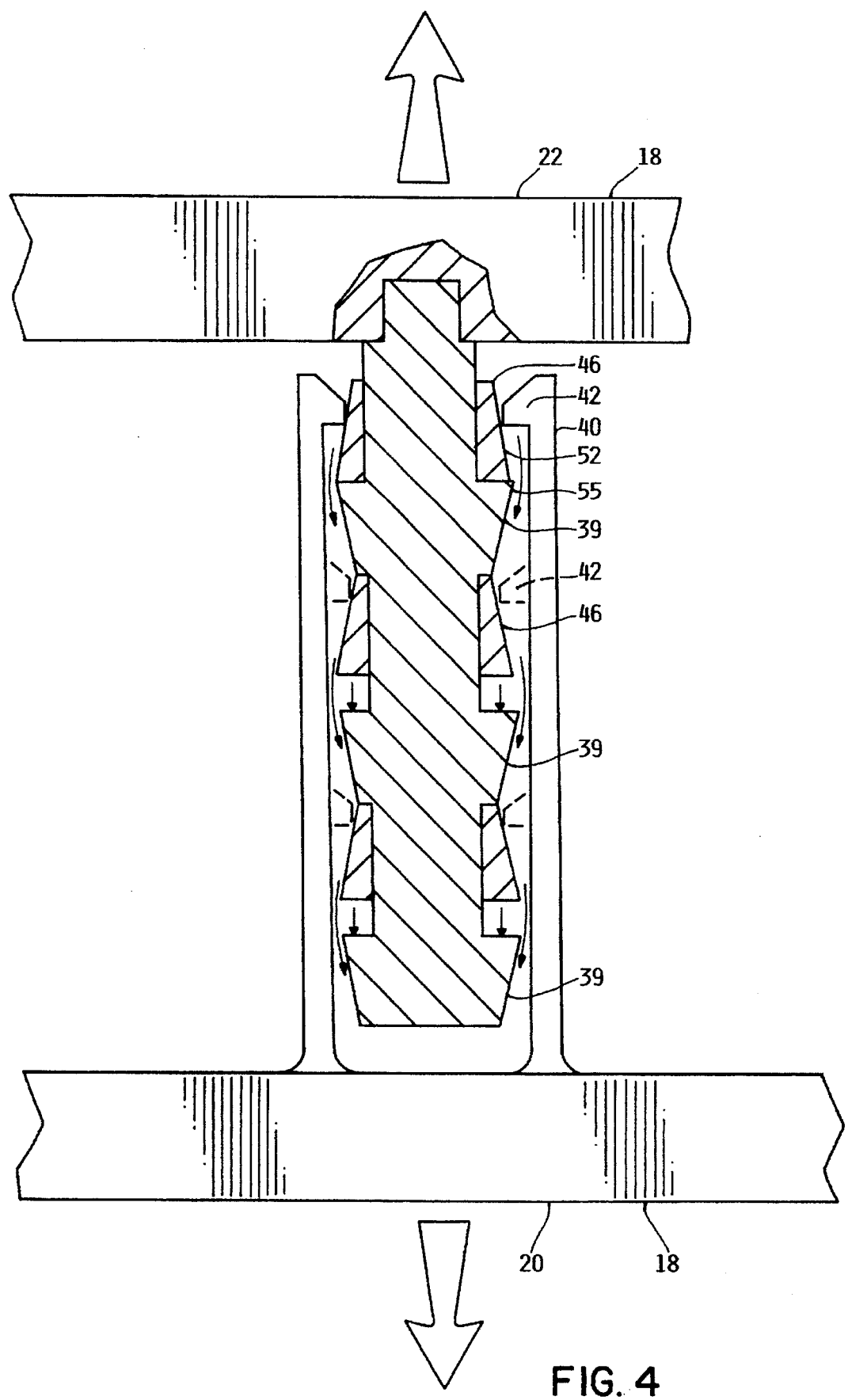
FIG. 4 is an alternate detail of the locking mechanism partially broken away, showing details of how the fingers and sleeves cooperate to completely unlock the medical instrument.

The sleeve means 46 may be frustoconical in cross-section, as shown in FIG. 2. The sleeve means 46 may be oriented on the projection 44 such that the outer walls 50 of the sleeve means 46 converge toward each other in the direction away from the fingers 40. In this manner, the outer walls 50 form a wedge 52.

In like manner, the head 39 may also be frustoconical in cross-section and may be oriented on the projection 44 such that the outer walls 54 of the head 39 converge toward each other in the direction toward the fingers 40, thus forming a wedge 55.

As will be described below, the wedge 52 and the wedge 55 meet during disengagement of the fingers 40 to form a smooth surface over which the hooks 42 may pass.

To lock a needle into the medical instrument 10, the physician places the open jaws 12 around the needle and squeezes the handles 18 together. As the handles 18 move toward each other, the hooks 42 slide along the wedge 55 of the head 39 closest to the first handle 20. The hooks 42 then engage the first shoulder 48.

If additional closing pressure or tension is required to hold the needle firmly in the holder 10, the physician continues to squeeze the handles 18 together, causing the hooks 42 to disengage from the shoulder 48 and pass over the wedge 52 of the first sleeve 46, and over the wedge 55 of the next head 39 until the next shoulder 48 is reached. This process continues until the desired tension is reached. The physician then releases pressure from the handles 18, and the hooks 42 are held against the shoulder 48 by the spring 26.

Figure 3:
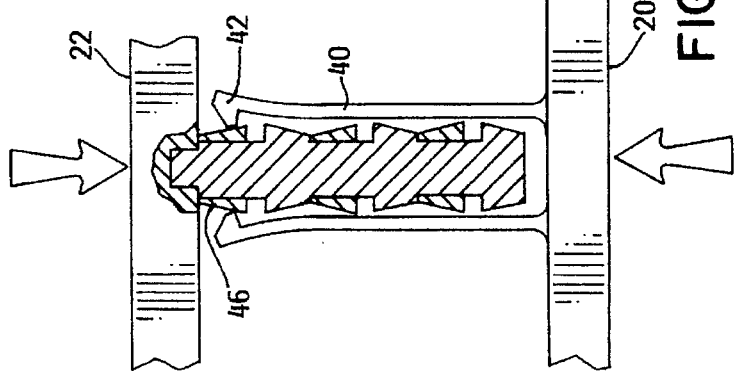
FIG. 3 is an alternate detail of the locking mechanism partially broken away, showing details of how the fingers are unlocked by pressing the handles toward one another.

To release the needle from the holder 10, the physician squeezes the handles 18 toward each other, most preferentially at the indentations 58. Enough pressure is exerted so that the fingers 40 move onto the sleeve means 46 nearest their point of engagement as seen in FIG. 3. Because the fingers 40 are flexible, they deflect outwardly as they move onto the sleeve means 46.

The physician then releases pressure on the handles 18. The fingers 40, having moved onto the sleeve means 46, now grasp this movable sleeve 46 as the handles 18 move away from each other under spring force due to the spring 26 or jaw end 14 tension. As seen in FIG. 3, the hooks pull the sleeve 46 toward the head 39 until the sleeve 46 abuts the next head 39, at which point the wedge 52 forms a smooth surface with or is slightly higher than the wedge 55. As the handles continue to move away from each other, the fingers 40, as shown by the arrows, move over the surface, past the head 39, and onto the next sleeve 46. The hooks 42 (shown in phantom) grasp the next sleeve 46, pull the sleeve 46 toward the next head 39 until the sleeve 46 abuts the head 39, and the fingers move over the smooth surface formed by this junction. The above process continues until the hooks 42 have disengaged from all heads 39. Then the handles 18 may be moved completely away from each other, releasing the needle.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. I claim, a medical instrument for one-handed operation, comprising:

(a) a pair of pivotally-connected scissor jaws having jaw ends and attachment ends, said jaw ends being used for grasping an object;

(b) a pair of spaced apart angularly opposed handles, comprising a first handle and a second handle, each handle having first ends and second ends, said first ends being secured to and in tandem with said attachment ends of said pair of scissor jaws; and (c) a releasable lock means mounted between said handles operable by one hand to lock and unlock said scissor jaws against said object by manipulating said handles toward each other without substantial lateral motion of said instrument, said releasable lock means comprising a finger means secured to the first handle, a holding means secured to the second handle, and a cooperating means for releasably engaging the finger means and the holding means permitting the first and second handles to move toward and away from each other in a series of steps to provide a tension adjustment between the first and second handles.

2. I claim, the medical instrument of claim 1 further comprising a spring biased against said handles for keeping said jaws open and said handles spread apart when at the at-rest position.

3. I claim, the medical instrument of claim 1, wherein said cooperating means assist in holding the first and second handles adjacent each other when the scissor jaws are retained in the closed position and assist in the release of the finger means from the holding means when the first and second handles are moved away from each other and the scissor jaws move to the open position.

4. I claim, the medical instrument of claim 3, wherein the holding means engage the finger means to hold the first and second handles adjacent each other, said cooperating means comprising sliding means to release the finger means from the holding means allowing the first and second handles to move away from each other.

5. I claim, the medical instrument of claim 4, said finger means further comprising a pair of flexible fingers having hooks, said holding means comprising a head engageable with the hooks to hold the first and second handles adjacent each other, said cooperating means being operable to release the hooks from the head when the first and second handles are moved toward each other.

6. I claim, the medical instrument of claim 5, said holding means comprising a plurality of said heads and a plurality of said cooperating means, thereby forming a tension adjustment which allows the first and second handles to be moved toward each other in a series of steps and said cooperating means being operable to release the hooks from all heads when the first and second handles are moved toward each other.

7. I claim, the medical instrument of claim 1, said releasable lock means further comprising a projection secured to the second handle, a head mounted on said projection, said finger means engageable with said head to hold the first and second handles adjacent each other, and sleeve means surrounding said projection adapted to be engaged by said finger means to release the finger means from said head on movement of the finger means onto said sleeve means whereby the first and second handles move away from each other to release said scissor jaws.

8. I claim, the medical instrument of claim 7, said finger means comprising a pair of flexible fingers having hooks, said head having a shoulder engageable with the hooks to hold the first and second handles adjacent to each other, said sleeve means being spaced from said shoulder to allow the hooks to engage the shoulder, said hooks being moveable onto the sleeve means to disengage the hooks from the shoulder to allow the first and second handles to move away from each other.

9. I claim, the medical instrument of claim 8, said sleeve means being frusto-conical in cross section having outer walls converging toward each other in the direction away from the fingers and forming a wedge over which said hooks ride to disengage said hooks from said shoulder, and said head is frusto-conical in cross section, having first walls of said head converging toward each other in the direction toward the fingers and forming a wedge over which said hooks ride to complete disengagement of the hooks from said shoulder.

10. I claim, the medical instrument of claim 9, further comprising a plurality of hook-engaging heads adjusted for releasable engagement to said sleeve means thereby forming a tension adjustment which allows the first and second handles to be moved toward each other in a series of steps and said sleeve means being operable to release the hooks from all heads when the first and second handles are moved toward each other.

11. I claim, a medical instrument for one-handed operation, comprising:

(a) a pair of pivotally-connected scissor jaws having jaw ends and attachment ends, said jaw ends being used for grasping an object;

(b) a pair of spaced apart angularly opposed handles, comprising a first handle and a second handle, each handle having first ends and second ends, said first ends being secured to and in tandem with said attachment ends of said pair of scissor jaws;

(c) a spring, biased against said handles, for keeping said jaws open and said handles spread apart when at the at-rest position; and (d) a releasable lock means mounted between said handles operable by one hand to lock and unlock said scissor jaws against said object by manipulating said handles toward each other without substantial lateral motion of said instrument, said releasable lock means comprising, a finger means secured to the first handle, a holding means secured to the second handle, and a cooperating means for releasably engaging the finger means and the holding means, permitting the first and second handles to move toward and away from each other in a series of steps to provide a tension adjustment between the first and second handles.

12. I claim, the medical instrument of claim 11, wherein said cooperating means assist in holding the first and second handles adjacent each other when the scissor jaws are retained in the closed position and assist in the release of the the finger means from the holding means when the first and second handles are moved away from each other and the scissor jaws move to the open position.

13. I claim, the medical instrument of claim 12, wherein the holding means engage the finger means to hold the first and second handles adjacent each other, said cooperating means comprising sliding means to release the finger means from the holding means allowing the first and second handles to move away from each other.

14. I claim, the medical instrument of claim 13, said finger means further comprising a pair of flexible fingers having hooks, said holding means comprising a head engageable with the hooks to hold the first and second handles adjacent each other, said cooperating means being operable to release the hooks from the head when the first and second handles are moved toward each other.

15. I claim, the medical instrument of claim 14, said holding means comprising a plurality of said heads and a plurality of said cooperating means, thereby forming a tension adjustment which allows the first and second handles to be moved towards each other in a series of steps and said cooperating means being operable to release the hooks from all heads when the first and second handles are moved toward each other.

16. I claim, the medical instrument of in claim 11, said releasable lock means further comprising a projection secured to the second handle, a head mounted on said projection, said finger means engageable with said head to hold the first and second handles adjacent each other, and sleeve means surrounding said projection adapted to be engaged by said finger means to release the finger means from said head on movement of the finger means onto said sleeve means whereby the first and second handles move away from each other to release said scissor jaws.

17. I claim, the medical instrument of claim 16, said finger means comprising a pair of flexible fingers having hooks, said head having a shoulder engageable with the hooks to hold the first and second handles adjacent each other, said sleeve means being spaced from said shoulder to allow the hooks to engage the shoulder, said hooks being movable onto the sleeve means to disengage the hooks from the shoulder to allow the first and second handles to move away from each other.

18. I claim, the medical instrument of claim 17, said sleeve means being frusto-conical in cross section having outer walls converging toward each other in the direction away from the fingers and forming a wedge over which said hooks ride to disengage said hooks from said shoulder, and said head is frusto-conical in cross section, having first walls of said head converging toward each other in the direction toward the fingers and forming a wedge over which said hooks ride to complete disengagement of the hooks from said shoulder.

19. I claim, the medical instrument of claim 18, further comprising a plurality of hook-engaging heads adjusted for releasable engagement to said sleeve means thereby forming a tension adjustment which allows the first and second handles to be moved towards each other in a series of steps and said sleeve means being operable to release the hooks from all heads when the first and second handles are moved toward each other.

20. I claim, a medical instrument for one-handed operation, comprising:
   a) a pair of pivotally-connected scissor jaws having jaw ends and attachment ends, the jaw ends being used for grasping an object;
   b) a pair of spaced apart angularly opposed handles, comprising a first handle and a second handle, each handle having first ends and second ends, said first ends being secured to an in tandem with said attachment ends of said of pair of scissor jaws; and
   c) a releasable lock means mounted between said handles operable by one hand to lock and unlock said scissor jaws against said object by manipulating said handles toward each other without substantial lateral motion of said instrument, said releasable lock means comprising finger means secured to said first handle, said finger means comprising a pair of flexible fingers having hooks, a projection secured to the second handle, a head mounted on said projection, said head having a shoulder engageable with the hooks to hold the first and second handles adjacent to each other, said head being frustoconical in cross-section, having first walls of said head converging toward each other in the direction toward the fingers and forming a wedge over which said hooks ride to complete disengagement of the hooks from said shoulder, and sleeve means being frusto-conical in cross-section having outer walls converging toward each other in the direction away from the fingers and forming a wedge over which said hooks ride to disengage said hooks from said shoulder, said sleeve means surrounding said projection and being space from said shoulder to allow said hooks to engage said shoulder, said sleeve means being adapted to be engaged by said finger means to release the finger means from said head and the hooks from the shoulders on movement of the finger means onto said sleeve means whereby the first and second handles move away from each other to release said scissor jaws.

21. The medical instrument of claim 20, further comprising a plurality of hook-engaging heads adjusted for releasable engagement to said sleeve means thereby forming a tension adjustment which allows the first and second handles to be moved toward each other in a series of steps and said sleeve means being operable to release the hooks from all heads when the first and second handles are moved toward each other.

22. I claim, a medical instrument for one-handed operation, comprising:
   a) a pair of pivotally-connected scissors jaws having jaw ends and attachment ends, said jaw ends being used for grasping an object;
   b) a pair of spaced apart angularly opposed handles, comprising a first handle and a second handle, each handle having first ends and second ends, said first ends being secured to and in tandem with said attachment ends of said pair of scissor jaws;
   c) a spring, biased against said handles, for keeping said jaws open and said handles spread apart when at the at-rest position; and
   d) a releasable lock means mounted between said handles operable by one hand to lock and unlock said scissor jaws against said object by manipulating said handles toward each other without substantial lateral motion of said instrument, said releasable lock means comprising finger means secured to said first handle, said finger means comprising a pair of flexible fingers having hooks, a projection secured to the second handle, a head mounted on said projection, said head having a shoulder engageable with the hooks to hold the first and second handles adjacent to each other, said head being frustoconical in cross-section having first walls of said head converging toward each other in the direction toward the fingers and forming a wedge over which said hooks ride to complete disengagement of the hooks from said shoulder, and sleeve means being frusto-conical in cross-sectioned having outer walls converging toward each other in the direction away from the fingers and forming a wedge over which said hooks ride to disengage said hooks from said shoulder, said sleeve means surrounding said projection and being spaced from said shoulder to allow said hooks to engage said shoulder, said sleeve means being adapted to be engaged by said finger means to release the finger means from said head and the hooks from the shoulders on movement of the finger means onto said sleeve means whereby the first and second handles move away from each other to release said scissor jaws.

23. I claim the medical instrument of claim 22, further comprising a plurality of hook-engaging heads adjusted for releasable engagement to said sleeve means, thereby forming a tension adjustment which allows the first and second handles to be moved toward each other in a series of steps and said sleeve means being operable to release the hooks from all heads when the first and second handles are moved toward each other.

* * * * *

UNITED STATES PATENT AND TRADEMARK OFFICE
CERTIFICATE OF CORRECTION

PATENT NO. : 5,653,729
DATED : August 5, 1997
INVENTOR(S) : Michael C. Chappuis and Robert C. Collins It is certified that error appears in the above-identified patent and that said Letters Patent is hereby corrected as shown below:

Column 3, line 37, delete "are".

Column 7, line 22, delete "an" and insert --and--.

Column 7, line 45, delete "space" and insert --spaced--.

Signed and Sealed this

Sixth Day of January, 1998

*Attest:*

BRUCE LEHMAN

*Attesting Officer*     *Commissioner of Patents and Trademarks*